United States Patent [19]

Eoga

[11] Patent Number: 4,857,224

[45] Date of Patent: * Aug. 15, 1989

[54] MONOPERSULFATE-CONTAINING CLEANSERS

[75] Inventor: Anthony B. J. Eoga, Boonton, N.J.

[73] Assignee: Warner-Lambert Company, Morris Plains, N.J.

[*] Notice: The portion of the term of this patent subsequent to Dec. 7, 1999 has been disclaimed.

[21] Appl. No.: 314,604

[22] Filed: Feb. 23, 1989

Related U.S. Application Data

[63] Continuation of Ser. No. 594,085, Mar. 28, 1984, abandoned.

[51] Int. Cl.[4] .......................... C11D 7/18; C11D 7/10; C11D 17/00
[52] U.S. Cl. ..................................... 252/99; 252/174; 252/174.23; 252/186.31; 252/DIG. 2; 252/188.23
[58] Field of Search ..................... 252/99, 174, 174.23, 252/186.31, 186.32, 188.2, 188.23, DIG. 2; 264/118, 120, 122

[56] References Cited

U.S. PATENT DOCUMENTS 4,362,639 12/1982 Eoga ..................................... 252/99
4,405,486 9/1983 Eoga ..................................... 252/99

*Primary Examiner*—Paul Lieberman
*Assistant Examiner*—John F. McNally
*Attorney, Agent, or Firm*—Daniel A. Scola, Jr.; Charles A. Gaglia, Jr.; Henry C. Jeanette

[57] ABSTRACT

An improved denture cleansing composition is prepared comprising a pre-granulation of anhydrous perborate using polytetrafluorethylene as a compacting aid, in combination with a monopersulfate. The composition can be tableted on a high speed tableting press and packaged using conventional foil packaging equipment without tablet fracture or chipping.

20 Claims, No Drawings

MONOPERSULFATE-CONTAINING CLEANSERS

This is a continuation of copending application Ser. No. 06/594,085 filed on Mar. 28, 1984 now abandoned.

This invention relates to improved monopersulfate-containing cleansing compositions which have excellent cleaning properties and which can be easily tableted and packaged using high speed equipment. In a preferred embodiment it relates to denture cleansing compositions.

Tableted denture cleansing compositions are well known in the art. Traditionally, these compositions have contained a variety of sulfate salts, such as bisulfates, monopersulfates, and sulfates as detergents, oxidizers and the like, and have also utilized alkali metal and alkaline earth metal halides as bleaches. Such compositions have also included perborate, carbonate and phosphate salts in varying amounts, to provide effervescence and activation. Representative examples of cleansing compositions covering these various materials are set forth in U.S. Pat. Nos. 3,337,466, 3,704,227 and 4,362,639.

In the instance where the cleansing compositions mentioned above contain one or more perborate salts, and the compositions are prepared into tablets by compression, the compositions have presented certain drawbacks in that they are difficult to compress, and the resulting tablets lack mechanical strength. These problems are owing primarily to physical properties of the perborate salts employed. In particular, anhydrous sodium perborate, which has been utilized in the prior art denture cleansing compositions, is commercially available as a fluffy powder having a low specific weight and density and therefore resistant to compaction and agglomeration. To a much lesser extent, this same difficulty is experienced with another perborate salt additive, sodium perborate monohydrate.

Prior attempts to remedy these deficiencies have focused upon the addition of greater amounts of standard tableting aids such as talc, sodium benzoate, and the like. The addition of greater amounts of these ingredients, however, while remedying the difficulties of initial processing and tablet formation, carry with them certain other drawbacks, namely that the formed tablets exhibit retarded action in use, that renders them less commercially desirable. In particular, the increased amounts of tableting aids tend to prolong the disintegration time of the tablet, with the result that the activity of the tablet is delayed and in some instances slightly suppressed, and therefore less attractive to potential consumers.

A process is disclosed in U.S. Pat. No. 4,115,519 to Brichard et al., for the manufacture of sodium perborate monohydrate, that purportedly results in the preparation of granules of the monohydrate possessing the desired particle size, specific weight, abrasion resistance and flowability sought for use in connection with the compaction of dental cleanser tablets. The technique disclosed by the patent, however, is complex and costly, and requires specialized apparatus to conduct a fluidized bed particle formation in contact with hydrogen peroxide. The patentees refer to prior art processes for the formation of the monohydrate salt, and indicate that those processes, as well, are complex and expensive, and frequently yield particles that are unsuitable for the present application.

U.S. Pat. No. 3,340,152, to Hotko, discloses that polyfluorocarbons may be utilized in the manufacture of tablets, as lubricants, and in amounts by weight of the tableting composition, ranging from about 1% to about 15% by weight, to supplant such known lubricants as magnesium stearate, sodium lauryl sulfate, polyethylene glycols and the like. Hotko suggests that the fluoropolymer may be added directly to the tableting mixture, in its capacity and amount as a lubricant, and purportedly has a favorable effect on the tablet-forming process. There is no disclosure in Hotko that the fluoropolymers would serve as agglomeration or compaction aids, to facilitate the preparation of granulated materials of increased and improved specific weight.

U.S. Pat. No. 4,409,118 discloses an effervescent cleansing composition in tablet form comprising (1) a phosphate salt in amounts of about 20% to about 45% by weight; (2) a silicate salt in amounts up to about 20% by weight; (3) at least one perborate salt in an amount of at least 50% by weight, wherein at least a portion of the perborate salt is in a compacted granulated mixture in an effective amount to facilitate compaction without substantially sticking to tablet forming equipment and with suitable dimensional stability and without prolonged disintegration when placed in solution. The granulated mixture contains from about 0.01% to about 0.7% by weight of said granulated mixture of a polymeric fluorocarbon.

While the problems of tableting have been focused on to some extent in the above prior art, they have not solved the problem of forming a tablet from a cleansing composition comprising the combination of monopersulfates with anhydrous perborates. Mixtures of anhydrous and monohydrate perborates have been successfully tableted in phosphate-containing compositions, such as those disclosed in U.S. Pat. No. 4,409,118 discussed above. Tablets made from compositions containing anhydrous and monohydrate perborates have not, however, contained monopersulfates since they have caused problems in high speed tablet processing such as fracture, chipping and crumbling. Tablets made from these ingredients have previously suffered from softness which was largely responsible for these problems.

The instant invention compositions are unique in solving the above-mentioned tableting problems. The inventive compositions additionally provide the efficacy of cleaning and speed of dissolution as required of tableted cleansers. Additionally, to have a commercial appeal, the solutions formed from these tableted compositions do not suffer from cloudiness. The tableted compositions remain clear below the surface foam when dissolving and do not leave a residue at the bottom of the solution container. Thus, the instant compositions accomplish all the requirements of a good cleanser while providing for the first time combining anhydrous perborates with monopersulfates in tablet form.

In particular, the cleaning compositions of the instant invention comprise:

(a) pre-granulated mixture of an anhydrous perborate, a perborate monohydrate and a polymeric fluorocarbon compound, the ratio of the anhydrous to the monohydrate being about 0.5:1 to about 1.75:1 and the polymeric fluorocarbon being present in amounts of about 0.05% to about 0.85% by weight of the pre-granulation; and (b) about 30% to about 65% by weight of a monopersulfate compound, based on the weight of the total cleansing composition.

The monopersulfates useful in the present invention may comprise alkali metal and alkaline earth metal monopersulfate salts. The alkali metal monopersulfate salts are preferred. Specifically potassium monopersulfate and sodium monopersulfate are among the preferred. The potassium salt is the most desirable and is preferably employed in the form of a triple salt with potassium bisulfate and potassium sulfate, e.g., $KHSO_5 \cdot KHSO_4 \cdot K_2SO_4$.

In the mole ratio of 2:1:1 the foregoing triple salt is known commercially by the trademark "OXONE®" and is sold by E. I. duPont DeNemours & Co., Inc.

As mentioned above the monopersulfate salt may be present in amounts of about 30% to about 65% by weight of the total cleansing composition, preferably in amounts of about 35% to about 60% and most preferably about 40% to about 55% by weight.

It is critical to the invention that the combination of monopersulfate and anhydrous perborates be in the present composition. In a preferred embodiment, however, monohydrate perborates are also present. The anhydrous and monohydrate perborates useful in the present invention may be selected from alkali metal perborates and alkaline earth metal perborates. More particularly, the sodium and potassium salts of anhydrous and monohydrate perborate are preferred, i.e. anhydrous sodium perborate and sodium perborate monohydrate.

The anhydrous perborate salts are generally present in amounts of at least about 1% by weight of the composition and preferably in about 5–7% by weight. The perborate monohydrate salts are generally present in amounts of about 0 to 15% by weight of the total compositions and preferably about 9 to about 12%.

The preparation of the compacted, granulated mixture of perborate salts with a polymeric fluorocarbon is also critical to the tableting aspect of the instant invention. The preparation of this compacted granular mixture and its employment in the present composition is particularly noteworthy as it facilitates the compaction of the perborate salt without adversely effecting the properties and activity of tablets prepared from the composition. Perborate salts, and in particular, anhydrous sodium perborate, are extremely light, fluffy materials having a low specific weight, that have been difficult to compact when attempts to incorporate this material in denture cleanser tablets, for example, have been made. Thus, the perborate component has tended to stick to the tablet dies, and tablets prepared with the perborate have been extremely frangible and therefore commercially undesirable. Prior art attempts to remedy this deficiency by the addition of greater quantities of conventional tableting aids, have resulted in the preparation of tablets, that while dimensionally stable and mechanically strong, exhibit greatly diminished activity when placed in solution. Thus, disintegration times are undesirably prolonged, and in some instances disintegration does not take place.

As discussed earlier herein, U.S. Pat. No. 3,340,152 to Hotko, describes the use of a polymeric fluorocarbon as a lubricant in tablet formation. Efforts to utilize the polymeric fluorocarbons disclosed by Hotko within the ranges set forth in the patent, proved fruitless, as the resulting tablets, while dimensionally stable, exhibited little or no activity in solution. Likewise, efforts to place even reduced amounts of the polymeric fluorocarbons in direct combination with the ingredients of cleansers such as those presently disclosed, resulted in the preparation of tablets having similar drawbacks. Accordingly, the preparation of the perborate salts in the manner disclosed in the present invention is important to the preparation of compositions in tablet form, that possess the property of dimensional stability and ease of preparation, in combination with retention of desirable solution activity. Thus, tablets prepared by the present invention disintegrate as quickly, and in some instances more quickly than acceptable denture tablets prepared in accordance with the prior art.

The mixture of the perborate salts with the polymeric fluorocarbon may include the fluorocarbon in an amount preferably ranging from about 0.33% to about 0.66% by weight of the perborate salt. The polymeric fluorocarbon may be selected from a well known group of polymeric and copolymeric substances made up of carbon and fluorine, which, in addition, may contain hydrogen and/or chlorine. The fluorocarbon may include at least one fluoroolefin; for example, polytetrafluoroethylene, copolymers of tetrafluoroethylene and hexafluoropropylene, and copolymers of vinylidene fluoride and hexafluoropropylene would be included. The preferred polymeric fluorocarbon comprises polytetrafluoroethylene.

The fluorocarbon polymers may be utilized in the form of powders having particle sizes acceptable for combination with the perborate salts, and preferably ranging up to about 150 microns in size. The exact particle size may vary, and an average particle size of from about 25 to about 75 microns may be used. The exact particle size of the polymeric fluorocarbon is not critical, however, to the practice of the present invention.

The preparation of the perborate salt-polymeric fluorocarbon mixture into compact granules may be conducted by compaction on a continuous or batch basis, by means, for example, of a roller compactor or a tablet slugging machine, to form a plurality of preforms such as flakes or slugs. Preforms would thereafter be subjected to comminution under agitation to form the desired particles, and may possess particle sizes ranging on the order of mesh of about 10 to about 20.

In addition to the ingredients set forth above, the present compositions may contain a variety of additional ingredients selected on the basis of desired end use. Thus, for example, the compositions may include detergent compounds, such as organic and inorganic detergents, including non-ionic detergents such as the various polyoxyethylene ethers of aromatic and aliphatic alcohols, as well as the polyoxyethylene ethers of hydrophobic propylene oxide polymers. Additionally, ethoxylated acids, and amines are also contemplated. The amount of the detergent is preferably about 0.4 to about 1% by weight and more preferably about 0.5 to about 0.6% by weight of the total cleansing composition. The limiting factor for amounts of detergent is that higher quantities prevent dissolution of the tablet and therefore reduce the effective cleaning time. These compounds assist in maintaining a foaming action in the instance where the cleansing compositions are placed in aqueous solution.

Also, the compositions may contain other adjuvant materials, that may be inorganic or organic in structure. Thus, inorganic water-soluble alkaline builders such as alkali and alkaline earth metal carbonates, hydroxides, and mixtures may be added. Particularly, sodium carbonate may be present in an amount of up to about 8% by weight, as it functions not only as a builder, but enhances effervescence and assists in stabilizing the pH of the solutions obtained from the composition.

The present compositions may also contain sequestrants for the purpose of maintaining solution clarity, in the instance where the compositions are placed in solution. The sequestrants may also assist in the inhibition of corrosion and tarnish of particles soaked in solutions containing the present compositions. Useful sequestrants include ethylene diamine tetracetic acid (EDTA) and its corresponding alkali salts, as well as other polyfunctional organic acids, such as citric acid, maleic acid and their corresponding salts. The sequestrants may be present in amounts of up to about 3% by weight.

In the instance where the composition is to be prepared for use as a denture cleanser, other additives such as flavorings, colorants, perfumes and the like may be added in various amounts, as is standard in the art. For example, the flavorings may include varieties of mint, oil of clove, artificial vanilla flavoring, and others. These materials may be included and blended in various combinations within the scope of the present invention. The choice of the required amounts is likewise within the skill of the art.

In the instance where the present cleansing compositions are formulated for use as denture cleansers, the colorants useful herein are those known as F.D.&C. and D.&.C. dyes and lakes. These materials are certified by the Federal Food and Drug Administration as acceptable for use in food, drug and cosmetic applications, and drug and cosmetic colorings. The materials acceptable for the foregoing spectrum of use are preferably water-soluble, and include indigoid dye, known as F.D.&C. Blue No. 2, which is the disodium salt of 5,5'indigotindisulfonic acid. Similarly, the dye known as F.D.&C. Green No. 1, comprises a triphenylmethane dye and is the monosodium salt of 4-[4-(N-ethyl-p-sulfobenzylamino)diphenylmethylene]-[1-(N-ethylN-p-sulfoniumbenzyl)-Δ2,5-cyclohexadienimine]. A full recitation of all F.D.&C. and D.&C. and their corresponding chemical structures may be found in the Kirk-Othmer Encyclopedia of Chemical Technology, at Volume 5, pages 857-884, which text is accordingly incorporated herein by reference. Dyes and colorants will fade at different rates and may be chosen to provide specific end points and fade times.

The foregoing colorants may be blended with each other in a variety of combinations. It is particularly desirable that the colorants be chosen so that the composition when initially dissolved will present a deep hue. This is important in the instance where the composition serves as a denture cleanser, as the fading phenomenon can signify the completion of cleaning.

The present cleansing compositions may also include other ingredients such as, pH adjustment additives, perfumes and the like, and are particularly useful when prepared in tablet form for use, for example, as denture cleansers.

The present invention also includes a method for the preparation of the inventive compositions, which comprises preparing at least a portion of the anhydrous perborate and monoperborate components as a first mixture, along with the polymeric fluorocarbon compound as a compaction aid, compacting this mixture and forming a pre-granulation or plurality of particles therefrom such that the particles are of a size which will pass through a standard U.S. screen size mesh of about 10 to about 20. The monopersulfate salt is then blended into the pregranulated mixture and the blend is then tableted.

Additional conventional ingredients not already mentioned in the above process may be combined with the monopersulfate salts to form a second mixture prior to final addition of the perborate/fluorocarbon granulation.

Tablets made from the above compositions using the above process exhibit excellent hardness on the average of at least 10 SCU, preferably about 14-16, but may be as much as 20 SCU. SCU is an abbreviation for Strong Carb Unit. Each SCU is equivalent to one Kilogram per square inch ($Kg/in^2$). It is critical that the hardness be such that chipping or fracture during processing and packaging be avoided. Ordinarily, it is difficult to maintain tablet structural integrity if the hardness is not at least 10 SCU (10 $Kg/in^2$). The present compositions with the above process steps provide such a tablet without the need for increased addition of excipients, tableting agents and the like. While such ingredients may be added, the amounts of these ingredients is reduced due to the favorable effect of the polymeric fluorocarbon present in the compacted granules of the perborate salt pre-granulation. Naturally, minor additional quantities of ingredients such as the polymeric fluorocarbon, may be made for their stated purpose, such as for lubrication and the like. Such additions, however, are not critical and do not form a part of the present invention.

Lubricants which may, however, be useful to insure good release of the tablet from the die are those well known in the art. For example, sodium lauryl sulfate, polyethylene glycols, talc and metal stearates are useful. Of these, the metal stearates are preferred. Illustrative, non-limiting examples of useful stearate lubricants are sodium stearate, calcium stearate, potassium stearate and magnesium stearate. Magnesium stearate is most preferred.

The amounts of metal stearate incorporated are usually minute, since excessive amounts tend to make cloudy aqueous solutions. Additionally, over-incorporation of metal stearates can prevent the tablet from dissolving within the reasonable dissolution time of cleaners, particularly of denture cleaners. Thus, metal stearates are generally used in amounts of about 0.025 to about 0.05% and preferably about 0.03% to about 0.04% by weight of the total composition.

A fuller understanding of the present invention will be gained from a review of the following illustrative examples. Unless specified otherwise, all amounts are expressed in percent by weight.

EXAMPLE I

Various compositions representative of the instant invention were prepared having the formulation shown in Table I. A pre-granulation of the anhydrous perborate and perborate monohydrate was prepared using polytetrafluoroethylene as the compacting aid. The constituents were blended for about 3 minutes and passed through a tablet slugging machine having 27/32 inch dies. The slugs were then passed through an oscillating granulater having a 16 mesh screen.

Potassium monopersulfate and standard additional ingredients were then blended with the pre-granulation and the blended mixture was pressed into tablets.

Each of the compositions in Table I were tableted and tested for their cleaning ability on test tiles which had been treated with a combination of plaque and various food stains. The stains were caused by a mixture of coffee, tea, blueberry pie and grapefruit juice. The plaque was grown overnight at 37° C. Staining of the tiles was accomplished overnight at 23° C.

Composition IV was representative of a typical prior art composition since it did not have the monopersulfate salt, but rather contained only the phosphate salt.

Compositions I, II, III, V and VI were representative of the inventive compositions. A control composition, whose formulation is not shown, was used as a comparison to compositions I-VI. The control formulation did not contain the perborates/polytetrafluoroethylene pre-granulation in combination with the monopersulfate. Rather the control contained only the monopersulfate salt, the sodium perborate monohydrate, but not anhydrous perborate. Obviously the control did not have the Applicant's pre-granulation either.

Each test tablet was placed in a beaker containing a stained tile in 120 ml of water at 45° C. Composition I showed results in 5 minutes which were equal to or better than the control results in 12 minutes. Formulations II, III, V and VI were also superior in cleaning efficacy to the control. Composition IV required the same time as the control (12 minutes) to clean the tiles as well as compositions I-III, V and VI did in 5 minutes.

TABLE I

| Denture Cleansing Compositions | | | | | | |
|---|---|---|---|---|---|---|
| | I | II | III | IV | V | VI |
| Pre-granulation A | | | | | | |
| Sodium Perborate Anhydrous | 296.1 | 236.9 | 181.7 | 675 | 181.7 | 145.4 |
| Sodium Perborate Monohydrate | 181.7 | 145.4 | 296.1 | 1100 | 296.0 | 236.9 |
| Polytetrafluoroethylene | 2.2 | 1.7 | 2.2 | 8 | 2.2 | 1.7 |
| Final Mixture | | | | | | |
| Sodium Carborate | 300.0 | 240.0 | 250.0 | — | 300.0 | 240.0 |
| Potassium Monopersulfate | 1880.0 | 1304.0 | 1880.0 | — | 1880.0 | 1540.0 |
| Ethylenediaminetetracetic Acid (Tetrasodium salt) | 25.0 | 20.0 | 25.0 | 100 | 25.0 | 20.0 |
| Detergent | 20.0 | 16.0 | 15.0 | 15 | 20.0 | 16.0 |
| Pregranulation A | 480.0 | 384.0 | 480.0 | 1783 | 480.0 | 384.0 |
| Sodium Tripolyphosphate Anhydrous | 480.0 | 384.0 | 480.0 | — | 480.0 | 384.0 |
| Trisodium Phosphate | — | — | — | 1000 | — | — |
| Magnesium Stearate | 1.0 | 0.8 | 1.0 | — | 1.0 | 0.8 |
| Polytetrafluoroethylene | 20.0 | 16.0 | 20.0 | 5 | 20.0 | 16.0 |
| Fragrance | 15.0 | 12.0 | 15.0 | 15 | 15.0 | 12.0 |
| Color | 0.9 | 0.9 | 0.9 | 5.8 | 0.9 | 0.9 |
| Hardness (SCU) | 12-13 | 11-12 | 12-13 | 15 | 12-13 | 12-13 |

EXAMPLE II

This example demonstrates that on anhydrous perborate pre-granulation in combination with monopersulfate can be compressed into a tablet using high speed equipment without the fracture problems of the prior art.

All the compositions of Example I were put into a high speed tablet machine capable of producing 900-1000 tablets per minute. The tablets were then pressed at this speed and packaged on a standard high speed foil packaging machine. All formulations containing the inventive combination (I, II, III, V and VI) were successfully tableted & packaged without chipping or tablet fracture. Composition IV, however, which did not contain the inventive combination, broke apart in the tableting machine and could not be successfully packaged as a commercial product.

EXAMPLE III

The inventive compositions of Example I were tableted on high speed tableting machines at approximately 900-1000 tablets per minute and packaged on a standard foil packaging machine.

When the compositions of Example I were prepared without the use of pre-granulation "A," they could not be tableted on a high speed tableting press. The tablets capped and broke apart easily upon exiting from the tablet press. Composition I without the use of pre-granulation "A" was successfully tableted on slow speed tableting press at the rate of 340-400 tablets per minute, but these tablets suffered from an unacceptable hardness of about 5 to 8 SCU. Attempts to use a conventional foil packaging machine to package the tablets failed due to an excessive number of tablet fracture during the process.

It is evident that in order to effectively prepare a composition containing both monopersulfate and anhydrous perborate, pre-granulation "A" is an essential step if the formulation is to be successfully tableted on high speed tableting presses and foil packaged in conventional foil packaging machines.

The invention being thus described, it will be obvious that the same may be varied in many ways. Such variations are not to be regarded as a departure from the spirit of scope of the invention and all such modifications are intended to be included within the scope of the claims.

What is claimed is:

1. A cleansing composition in tablet form especially useful for cleaning dentures comprising:
   (a) a pre-granulated mixture of an anhydrous perborate, a perborate monohydrate and a polymeric fluorocarbon compound, the ratio of the anhydrous to the monohydrate being about 0.5:1 to about 1.75:1 and the polymeric fluorocarbon being present in amounts of about 0.05% to about 0.85% by weight of the pre-granulated mixture; and
   (b) about 30% to about 65% by weight of a monopersulfate compound, based on the weight of the total cleansing composition.

2. The composition of claim 1 wherein sodium carbonate is incorporated in amounts of about 8% to about 10% by weight of the total composition.

3. The composition of claim 1 wherein the monopersulfate is an alkali metal monopersulfate or an alkaline earth metal monopersulfate present in amounts of about 40 to about 50% by weight of the total composition.

4. The composition of claim 3 wherein the monopersulfate is potassium or sodium monopersulfate.

5. The composition of claim 3 wherein the perborates are selected from the group consisting of alkali metal perborates, alkaline earth metal perborates, mixtures thereof present in amounts of about 5% to about 15% of the total composition.

6. The composition of claim 5 wherein the anhydrous perborate is potassium or sodium anhydrous perborate.

7. The composition of claim 6 wherein the perborate monohydrate is potassium or sodium perborate monohydrate.

8. The composition of claim 7 wherein the polymeric fluorocarbon is polytetrafluoroethylene.

9. The composition of claim 7 wherein the polymeric fluorocarbon includes at least one fluoroolefin.

10. The composition of claim 1 further comprising at least one material selected from the following: builders, detergents, lubricants, sequestrants, perfumes, flavorings, colorings, excipients, disintegrants and mixtures thereof.

11. The composition of claim 10 wherein said sequestrant comprises ethylene diamine tetracetic acid and its alkali metal salts, and said builders include sodium carbonate.

12. A process for preparing a cleansing composition comprising
    (a) preparing a compacted mixture comprising anhydrous perborate salts and perborate monohydrate salts in combination with a polymeric fluorocarbon as a compacting aid compound; and
    (b) grinding said compacted mixture into a pre-granulation having a particle size which will pass through a standard screen with a mesh size of about 10 to about 20; and
    (c) blending the pre-granulation with a monopersulfate salt compound; and
    (d) forming the resultant blended mixture into a tablet.

13. The process of claim 12 wherein the polymeric fluorocarbon compound is polytetrafluoroethylene.

14. The process of claim 12 wherein said mixture is compacted by passing it through a roller compactor.

15. The process of claim 12 wherein said mixture is compacted by slugging.

16. The process of claim 13 wherein the anhydrous perborate salts and the monohydrate perborate salts are selected from the group consisting of alkali metal salts, alkaline earth metal salts and mixtures thereof.

17. The process of claim 16 wherein the anhydrous and monohydrate perborate salts are potassium or sodium.

18. The process of claim 12 wherein there is additionally added to the pre-granulation a material selected from the group consisting of builders, lubricants, detergents, sequestrants, perfumes, flavorings, colorings, excipients, disintegrants, and mixtures thereof.

19. The process of claim 18 wherein sodium carbonate is added in the amount of about 8% to about 10% by weight of the total composition.

20. A denture cleansing tablet having the composition of claim 7 and having a hardness of at least 10 $Kg/in^2$.

* * * * *